(12) United States Patent
Metcalf, Jr. et al.

(10) Patent No.: US 8,147,549 B2
(45) Date of Patent: Apr. 3, 2012

(54) ORTHOPEDIC IMPLANT WITH SENSOR COMMUNICATIONS ANTENNA AND ASSOCIATED DIAGNOSTICS MEASURING, MONITORING, AND RESPONSE SYSTEM

(75) Inventors: Newton H. Metcalf, Jr., Memphis, TN (US); Greg C. Marik, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 644 days.

(21) Appl. No.: 12/276,630

(22) Filed: Nov. 24, 2008

(65) Prior Publication Data

US 2010/0131067 A1   May 27, 2010

(51) Int. Cl.
*A61F 2/44* (2006.01)
(52) U.S. Cl. .................................... 623/17.11
(58) Field of Classification Search .............. 623/18.12, 623/23.16, 23.49, 24; 343/897
See application file for complete search history.

(56) References Cited

U.S. PATENT DOCUMENTS

| | | | |
|---|---|---|---|
| 2,750,321 A * | 6/1956 | Koppelman | 343/873 |
| 5,861,019 A | 1/1999 | Sun et al. | |
| 6,009,350 A | 12/1999 | Renken | |
| 6,093,205 A * | 7/2000 | McLeod et al. | 623/17.16 |
| 6,636,769 B2 | 10/2003 | Govari et al. | |
| 6,804,561 B2 | 10/2004 | Stover | |
| 7,023,391 B2 | 4/2006 | Wuidart et al. | |
| 7,083,104 B1 | 8/2006 | Empedocles et al. | |
| 7,218,232 B2 | 5/2007 | DiSilvestro et al. | |
| 2002/0042637 A1 | 4/2002 | Stover | |
| 2002/0095195 A1 | 7/2002 | Mass et al. | |
| 2003/0216793 A1 | 11/2003 | Karlsson et al. | |
| 2004/0112964 A1 | 6/2004 | Empedocles et al. | |
| 2004/0176811 A1 | 9/2004 | Von Arx et al. | |
| 2005/0012617 A1 | 1/2005 | DiSilvestro et al. | |
| 2005/0134452 A1 | 6/2005 | Smith | |
| 2005/0134520 A1 | 6/2005 | Rawat et al. | |
| 2005/0149139 A1 | 7/2005 | Plicchi et al. | |
| 2005/0154428 A1 | 7/2005 | Bruinsma | |
| 2005/0199731 A9 | 9/2005 | Empedocles et al. | |
| 2006/0009856 A1 | 1/2006 | Sherman et al. | |
| 2006/0069447 A1 * | 3/2006 | DiSilvestro et al. | 623/23.16 |
| 2006/0142820 A1 | 6/2006 | Von Arx et al. | |
| 2006/0147487 A1 | 7/2006 | Henderson | |
| 2006/0237537 A1 | 10/2006 | Empedocles et al. | |
| 2006/0241724 A1 | 10/2006 | Dublin et al. | |
| 2007/0052603 A1 | 3/2007 | Nyalamadugu | |
| 2007/0260294 A1 | 11/2007 | Schulman et al. | |
| 2007/0288065 A1 | 12/2007 | Christman et al. | |
| 2007/0288066 A1 | 12/2007 | Christman et al. | |

* cited by examiner

*Primary Examiner* — Thomas J Sweet
*Assistant Examiner* — Brian Dukert (57) ABSTRACT

A diagnostic system is provided that occupies a small area, provides sensing and transmitting of various diagnostic indicia, and with the aid of a healthcare professional, diagnoses and responds to such measurements. In the context of the spine, the diagnostic system comprises a spinal implant situated between two adjacent vertebrae, an antenna for sending and/or receiving signals to and/or from a remote location, a sensor for measuring at least one diagnostic condition, an activating element that has the ability to affect the at least one diagnostic condition, a power source to provide power to the diagnostic system, and a network that electrically connects the antenna, sensor, activating element and battery source.

16 Claims, 6 Drawing Sheets

ORTHOPEDIC IMPLANT WITH SENSOR COMMUNICATIONS ANTENNA AND ASSOCIATED DIAGNOSTICS MEASURING, MONITORING, AND RESPONSE SYSTEM

TECHNICAL FIELD

The invention relates generally to the field of measuring, monitoring, diagnosing and responding to various diagnostic conditions inside the human body, and more particularly, inside an orthopedic implant.

BACKGROUND

Surgical procedures are, for the most part, invasive procedures. That is, when a surgeon needs to operate on the part of the human body, it is advantageous to not have to perform the same or similar procedure twice. Nevertheless, this sometimes occurs for a variety of reasons. For example, in the context of the spine and spinal implants, the environment is a constantly shifting one. Particularly in the context of spinal disc implants, there is a variety of body parts and fluids that result in changing anatomy that can result in the need to perform a second surgery, e.g., to make adjustments or replacements to the spinal implant due to a changing environment around the implant since it was introduced in the disc space.

To avoid subsequent surgeries after an implant surgery, there is, therefore, a need to measure various diagnostic conditions (or indicia) inside the spinal implant (or surrounding area). With such measurements, a doctor or surgeon can thereby determine a need for a "second surgery," be it a modification or replacement. Ideally, however, the best case scenario is to avoid second or subsequent surgeries. Accordingly, a device that can perform monitoring, diagnosing and most importantly, also respond to such measurements, would be in great demand. Naturally, a device that can do all of the above function in or around a spinal implant would be in beneficial, but there also would be demand for such a system in the human body, or more particularly, inside an orthopedic implant.

One of the problems, however, is the ability to communicate the measurements of the various diagnostic indicia taken inside the body to the doctor or surgeon that is located outside the body, and ideally, to do this remotely. There, therefore, is a need for the ability to remotely transmit measurements of various diagnostic indicia from areas such as spinal implants to areas such as receivers outside the body.

Today, it is possible to manufacture a system that occupies a small area that transmits communications. For example, by using microelectronic substrate materials and nanowires one can manufacture an antenna, which can be used for the transmission of radio frequency (RF) signals. Also, it is possible to create small lightweight sensors that occupy very little space. As mentioned above in the context of a medical setting, however, there is a need for not only sensing and transmitting various diagnostic indicia in small and confined areas, but also diagnosing and responding to such measurements. Further, as mentioned above, if this can be accomplished remotely, a subsequent surgery or surgeries, and the costs and risks that come with them, can be avoided.

SUMMARY

A diagnostic system for a spinal implant is provided. The system comprises a spinal implant situated between two adjacent vertebrae, an antenna located in, on or adjacent to the spinal implant for sending and/or receiving signals to and/or from a remote location, a sensor located in, on or adjacent to the spinal implant for measuring at least one diagnostic condition in, on or adjacent to the implant, an activating element (or activator) located in, on or adjacent to the spinal implant that has the ability to affect the at least one diagnostic condition, a power source located in, on or adjacent to the spinal implant to provide power to the diagnostic system, and a network that electrically connects the antenna, sensor, activating element and battery source. As such, the diagnostic system of the present invention is designed occupy a small area, provide sensing and transmitting of various diagnostic indicia, and with the aid of a healthcare professional, diagnose and respond to such measurements.

In certain embodiments, the antenna of the diagnostic system of the present invention is incorporated into a material that can be integrated into the spinal implant. In some embodiments, the antenna may be woven or interlaced in a fabric material. In such embodiments, the antenna and fabric material may be incorporated into the spinal implant. In some embodiments, the implant itself may be made of a flexible material.

With the present invention, the at least one diagnostic condition that is measured, monitored and affected may be many different conditions or indicia, e.g., any one of the following indicia: loading information, pressure information, tension information, motion information, alignment or misalignment information, or temperature. In certain embodiments, the activating element is such that the diagnostic system is capable of affecting the at least one diagnostic condition incrementally and/or in either direction. Examples of activating elements that can be used with the present invention in the context of a spinal device may include a hydrostatic pump or a shape memory alloy. In embodiments where the activating element is a shape memory alloy, the activating element may also include a device to increase temperature, so that such device is connected to the shape memory alloy and is controlled by the addition or subtraction of power or electrical signals.

The diagnostic system of the present invention also can be used outside the context of the spine, for example, elsewhere in the human body. Such a system comprises an implant situated in the human body, an antenna located in, on or adjacent to the implant for sending and/or receiving signals to and/or from a remote location, a sensor located in, on or adjacent to the implant for measuring at least one diagnostic condition in, on or adjacent to the implant, an activating element located in, on or adjacent to the implant that has the ability to affect the at least one diagnostic condition, a power source located in, on or adjacent to the implant to provide power to the diagnostic system, and a network that electrically connects the antenna, sensor, activating element and battery source.

A method of measuring and responding to a diagnostic condition also is provided. The method comprises providing a diagnostic system according to the present invention as described above. The method further comprises reading the sensing information from the remote receiver, i.e., after the sensor measures the diagnostic condition and this sensing information is routed via the network to the antenna where it is transmitted to a remote receiver, and responding to the sensing information by sending a signal to the diagnostic system, which is received by the antenna, where it is then routed to the activating element, which will perform a desired function to affect the diagnostic condition.

Additional aspects and features of the present disclosure will be apparent from the detailed description and claims as set forth below.

DETAILED DESCRIPTION

For the purpose of promoting an understanding of the principles of the present disclosure, reference is made to the specific embodiments illustrated in the drawings, and specific language is used to describe the embodiments. It is nevertheless understood that no limitation of the scope of the present disclosure is intended. Any alterations and further modifications of the described embodiments, and any further applications of the principles of the present disclosure as described herein, are fully contemplated, as would occur to one skilled in the art to which the invention relates.

As stated above, the purpose of the present invention is to provide a system that occupies a small area, but provides sensing and transmitting of various diagnostic indicia, and also diagnoses and responds to such measurements. In particular, in the context of a spinal implant surgery, the present invention will allow for a surgeon to monitor a patient after such surgery, and make adjustments to the device, all in the hopes of avoiding a subsequent surgery to correct or modify any changes that take place subsequent to the first surgery or to intentionally and remotely change diagnostic conditions inside the body.

Figure 1:
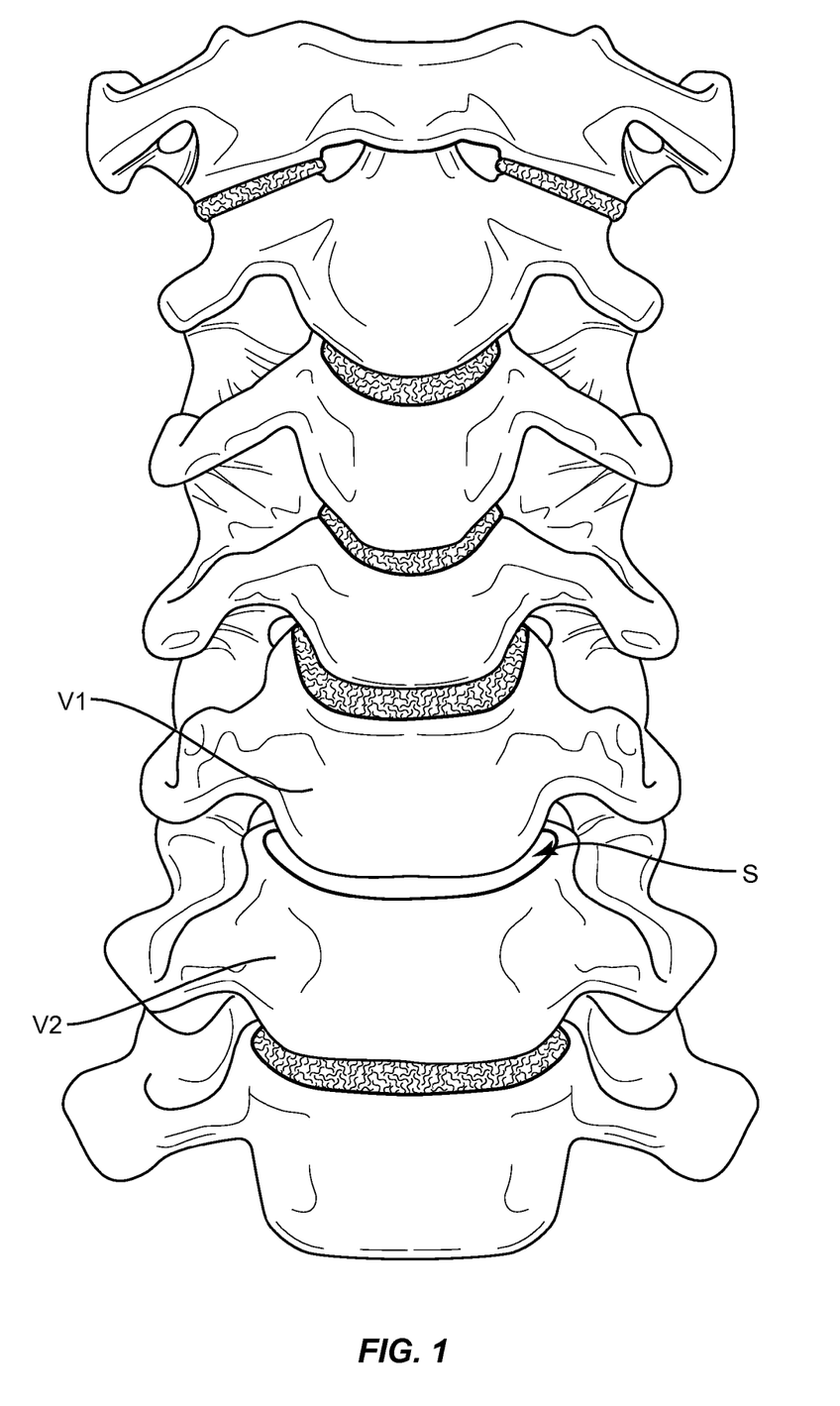
FIG. 1 shows a frontal view of a section of cervical spine, detailing the space between vertebral sections V1 and V2 after the disc between those sections has been removed.

FIG. 1 shows a frontal view of a section of cervical spine. In particular, FIG. 1 shows a section of cervical vertebrae after the disc between vertebral sections V1 and V2 has been removed. FIG. 1 also shows the space S between vertebral sections V1 and V2 where an artificial disc or spinal implant would be inserted during a spinal implant surgery. Further, such a system also may be used not only to avoid a subsequent surgery, but intentionally to remotely change diagnostic conditions inside the body.

Figure 2:
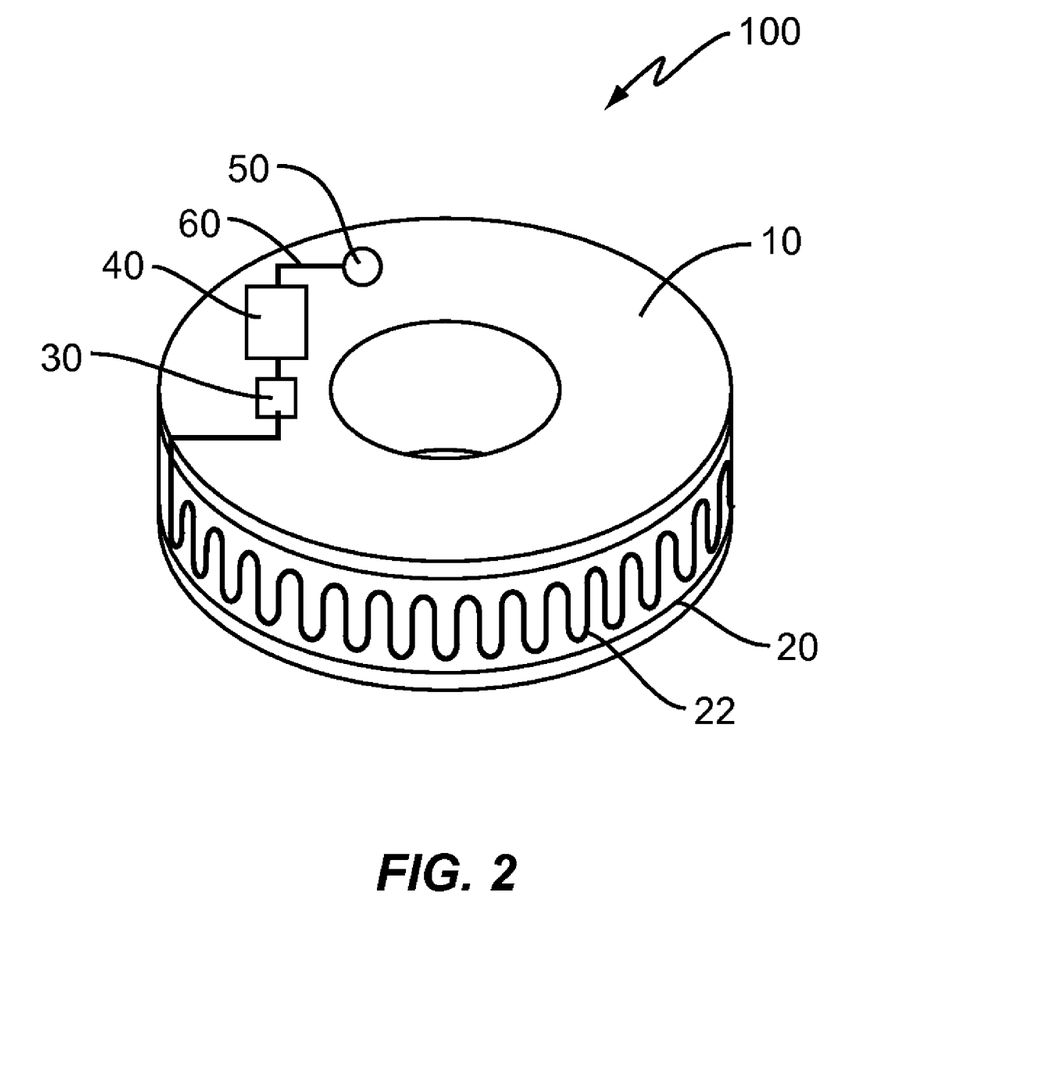
FIG. 2 shows an isometric view of one embodiment of the diagnostic measuring, monitoring and response system of the present invention.

FIG. 2 shows an isometric view of one embodiment of the diagnostic measuring, monitoring and response system 100 ("diagnostic system") of the present invention. The diagnostic system 100 of FIG. 2 comprises a nucleus implant 10, a fabric material 20, an antenna 22, a sensor 30, an activator 40, and a power source (or battery) 50. As shown in FIG. 2, the nucleus implant 10 is a donut shaped disc, but can be any shape to occupy the intervertebral disc space S, or even part of the disc space S. Alternatively, the nucleus implant 10 can represent an artificial disc-type device.

The antenna 22 is incorporated into the implant 10 in some fashion. In the embodiment of FIG. 2, the antenna 22 is a relatively thin wire or any other radio-conductive material that is wound several times on a woven or non-woven fabric material 20 of the implant 10. The material 20 need not necessarily be fabric, but needs to be able to receive and/or integrate the antenna 22, e.g., alternative flexible materials will be sufficient. For example, other suitable materials may include carbon fiber and polymers such as Polyetheretherketone ("PEEK"), polyethylene and polyurethane. As shown in FIG. 2, the thin wire of the antenna 22 is wound several times so that the antenna 22 can be relatively long even though it is placed on a relatively small implant 10, and in theory, a longer antenna 22 will be able to communicate better, i.e., send and receive signals more effectively.

The sensor 30 is placed somewhere in the implant 10, but in a location that is ideally suited for sensing the diagnostic conditions (indicia) the particular sensor 30 is intended to detect. That is, a sensor 30 such as the one of the diagnostic system 100 of FIG. 2 can be used to sense loading information on the implant 10 (i.e., the changing forces exerted on the implant 10 as it resides between the vertebral sections V1 and V2), pressure or tension information (i.e., the amount of pressure or tension at any given time that may be exerted on the implant 10, and in various locations on or inside the implant, depending on sensor 30 location), motion information (i.e., the extent to which the implant 10 may move around in the disc space S as it resides between the vertebral sections V1 and V2), alignment/misalignment information (i.e., its exact location or rather, how much distance, height, rotation, etc., the implant 10 may be not situated exactly as intended compared to its desired location for proper functioning), temperature (i.e., the temperature of the implant wherever the sensor 30 or other sensors 30 may be placed within or on the implant), and various other clinical measure that can be sensed.

Note that the sensor 30, as well as the activator 40, battery 50, and even the other elements are shown in FIG. 2 (as well as the counterpart components in FIGS. 3-6) primarily in a representational manner. That is, certain components are represented in block form, and will just as likely take on a different shape. Also, as noted, there may be several sensors 30, e.g., in different locations in the implant for measuring the various diagnostic indicia in the different locations of the implant 10, as well as on the implant. Further, note that as long as the sensor is connected to the diagnostic system through the network 60, which is preferably a simple electrical connection to carry power and signals, a sensor 30 may be located outside of the implant 10 for sensing certain diagnostic indicia there.

As shown in FIG. 2, the diagnostic system 100 also contains an activator 40. This activator or activating component may be any device that is capable of responding to the diagnostic indicia that is being sensed. That is, an activator 40 may be a device to change the loading, pressure or tension exerted on the implant 10. For example, a hydrostatic pump as the activator 40, when engaged, can increase the pressure on such an implant 10. Alternatively, an activator 40 may be a device that can somehow change the location of the implant 10, or a device that can somehow stabilize the implant, i.e., prevent the implant 10 from moving around the disc space S too much, such as a telescoping motor. Further, an activator 40 may be a device that corrects the alignment of the implant 40, such as individually-telescoping sides that allow for correction of a deformity. Even further, the activator 40 may be a device that can change the temperature of the implant 10, e.g., heat can be used to destroy nerve endings and potentially reduce pain and this can be accomplished with an exposed wire that is fed electricity from the power source 50. Materials that can be used to manufacture parts of the activator 40, e.g., parts of a hydrostatic pump can include stainless steel, Titanium ("Ti"), or Ti-6-4.

FIG. 2 also shows a power source 50. Typically, this will be some sort of biocompatible battery 50 that is suitable for small areas, and that can last over relatively long periods of time. Also, as stated above, the diagnostic system 100 of FIG. 2 also contains a network 60, which is preferably a simple electrical connection to carry the power from the power source 50 to the other components of the system, i.e., the activator 40 so it can perform the activating function or functions, the sensor 30 so it can perform the sensing functions, and the antenna 22 so it can receive and send signals.

As mentioned, the diagnostic system 100 of the present invention will allow for a surgeon to monitor a patient after such surgery, and make adjustments to the device, all in the hopes of avoiding a subsequent surgery to correct or modify any changes that take place subsequent to the first surgery or to intentionally and remotely change diagnostic conditions inside the body. In operation, after the diagnostic system 100 is implanted in the disc space S between intervertebral sections V1 and V2, the sensor can start sensing whatever diagnostic indicia it is designed to detect. This sensing information is then routed via the network 60 to the antenna 22 where it is transmitted to a remote receiver where it is received by a doctor or surgeon and diagnosed. In response to that sensing information, the surgeon can send a signal (or order) to the diagnostic system 100, which if such an order is necessary, will be received by the antenna 22. The antenna 22 will route the incoming signal (or order) to the activator 40, which will perform the action, or the response to the diagnosis, which was in response to the sensing. The sensing by the sensor 30 can be constant, and thus may be considered monitoring. Thus, the diagnostic system 100 provides a system for measuring (the sensing), monitoring, and response.

Figure 3:
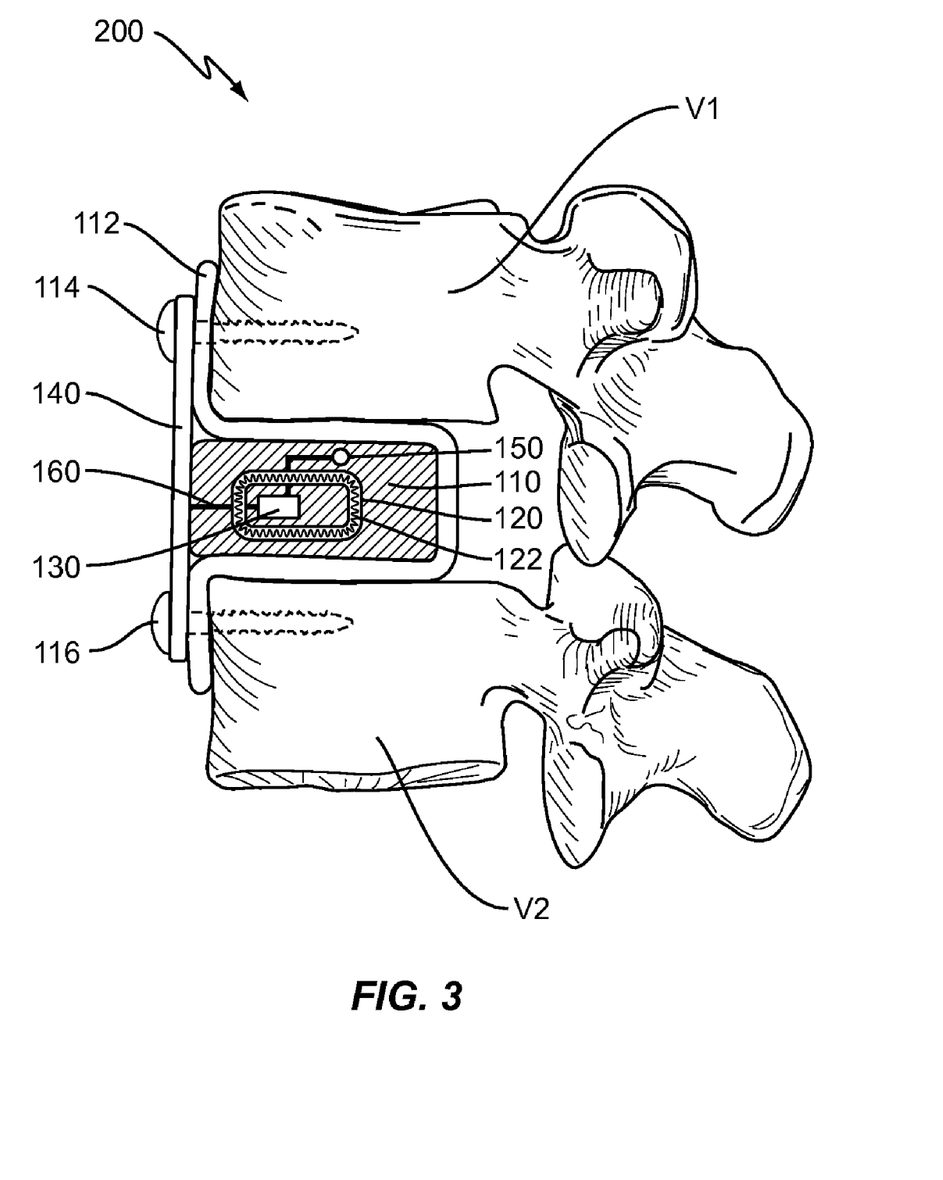
FIG. 3 shows a side view of another embodiment of the diagnostic measuring, monitoring and response system of the present invention.

FIG. 3 shows a side view of another embodiment of the diagnostic measuring, monitoring and response system 200 ("diagnostic system") of the present invention. The diagnostic system 200 of FIG. 3 comprises an implant 110, a fabric material 120, an antenna 122, a sensor 130, an activator 140, a power source 150, and a network 160 that electrically connects all of these components. As shown in FIG. 3, the implant 110 also is encapsulated (although not entirely) by a containment portion 112 and in part by the activator 140, which serves, in part, as a separate cover portion. Note, once again, that the implant 110 is not limited to the shape shown in FIG. 3, but may be any shape to occupy the intervertebral disc space S, or even part of the disc space S.

In the embodiment of the diagnostic system 200 of FIG. 3, the implant 110 (as well as other elements of the diagnostic system 200) is encapsulated by the containment portion 112, which serves several functions in this embodiment. That is, the containment portion 112 serves as a spinal plate by maintaining some degree of fusion between the vertebral sections V1 and V2. In this function, the containment portion 112 may be affixed to the respective vertebrae V1 and V2 by the use of screws 114 and 116, respectively, as shown in FIG. 3, just as a typical plate would be affixed. The containment portion 112, however, also serves to contain the implant 110 and other elements of the diagnostic system 200, as shown in FIG. 3. In addition, the containment portion 112 of diagnostic system 200 also helps the functioning of the diagnostic system 200 by providing a barrier or containment area to the implant 110. In this manner, the containment portion 112 may be made of any materials that can be used to make a typical spinal plate.

In the embodiment of FIG. 3, the implant 110 is made of, or at least, contains an adjustable material such as polyurethane. Other examples of material for the implant 110 can include PEEK, Polyester, or polyethylene. Further, the activator 140, which is separate from the containment portion 112, serves as a cover portion as well as the activator 140. In this manner, the activator 140 is made of a material that can "be activated" to thereby affect the implant 112 inside of the containment portion 112, and particularly and ultimately affect the desired diagnostic condition(s) of concern. For example, a preferred material for the activator 140 is a shape memory alloy that can be triggered to change shape with a concurrent change in temperature. One example of such material for the activator 140 is Nickel-Titanium ("NiTi").

Accordingly, in operation, the diagnostic system 200 of FIG. 3 will operate by the same principles as the diagnostic system 100 of FIG. 2. Diagnostic system 200 will allow for a surgeon to monitor a patient after such surgery, and make adjustments to the device, all in the hopes of avoiding a subsequent surgery to correct or modify any changes that take place subsequent to the first surgery or to intentionally and remotely change diagnostic conditions inside the body. In operation, after the diagnostic system 200 is implanted in the disc space S between intervertebral sections V1 and V2, the sensor 130 can start sensing whatever diagnostic indicia it is designed to detect. This sensing information is then routed via the network 160 to the antenna 122 where it is transmitted to a remote receiver where it is received by a doctor or surgeon and diagnosed. In response to that sensing information, the surgeon can send a signal (or order) to the diagnostic system 200, which if such an order is necessary, will be received by the antenna 122. The antenna 122 will route the incoming signal (or order) to the activator 140. Thus, the diagnostic system 200 provides a system for measuring (the sensing), monitoring, and response.

Figure 4:
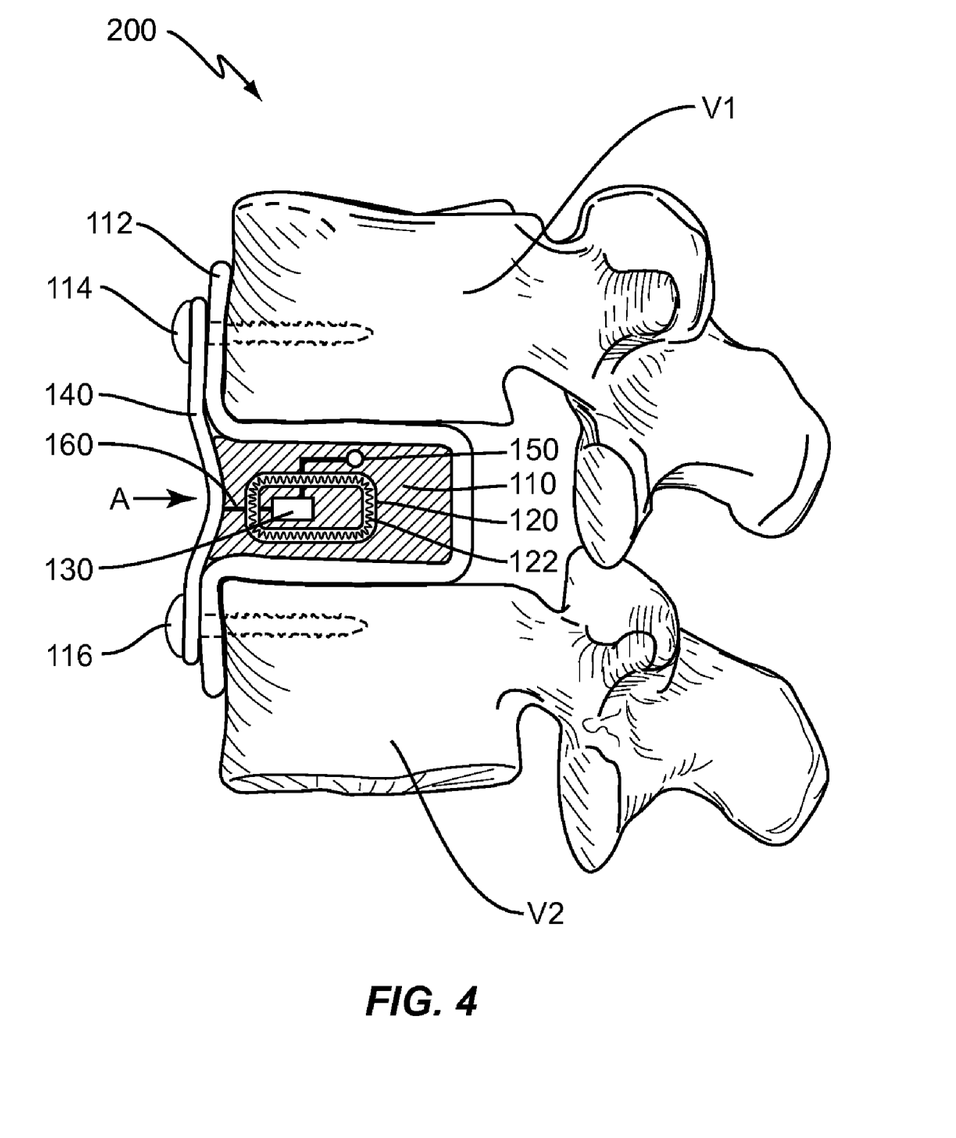
FIG. 4 shows a side view of the diagnostic system of FIG. 3 after the activator has been activated.

In the context of the diagnostic system 200 of the present invention, the typical sensing information may be, for example, loading exerted on the implant 110 or pressure information regarding how much pressure to which the implant is exposed. If it is diagnosed by the doctors or surgeons that there is more loading than expected on the implant 110 in its current state, then a signal can be sent to the system 200 that will make the activator 140 increase the pressure by causing the activator 140 to flex or bend inward toward the implant 110, as shown in FIG. 4 (with the arrow A depicting the direction of motion of the activator 140). If the activator 140 is a shape memory alloy, it will take on a particular shape when "ordered" to do so. For example, if more pressure is needed for the implant 110 to accomplish its desired task, the system 200 can increase the temperature of the activator 140 so that it will revert or take on its desired shape, as shown in FIG. 4. It is because of the change in shape of the activator 140 that it is desirable to have the implant 110 to be composed of flexible material, i.e., so it can react to and adjust with the activator 140.

Note that for increasing the temperature of the activator 140, although not shown in the Figures, there may be a direct connection of the network 160 between the power source 150 and the activator 140. Alternatively, there may be an additional element or component (not shown) that is part of the diagnostic system 200 that helps increase the temperature of the activator 140. The additional component may be inside or outside of the activator 140, or merely connected to it. For example, the order that comes into the antenna 122 may direct the battery source 150 to send a power signal to this additional component so that it will help the activator increase (or decrease) in temperature merely by being part of, or connected to the activator 140.

Figure 5:
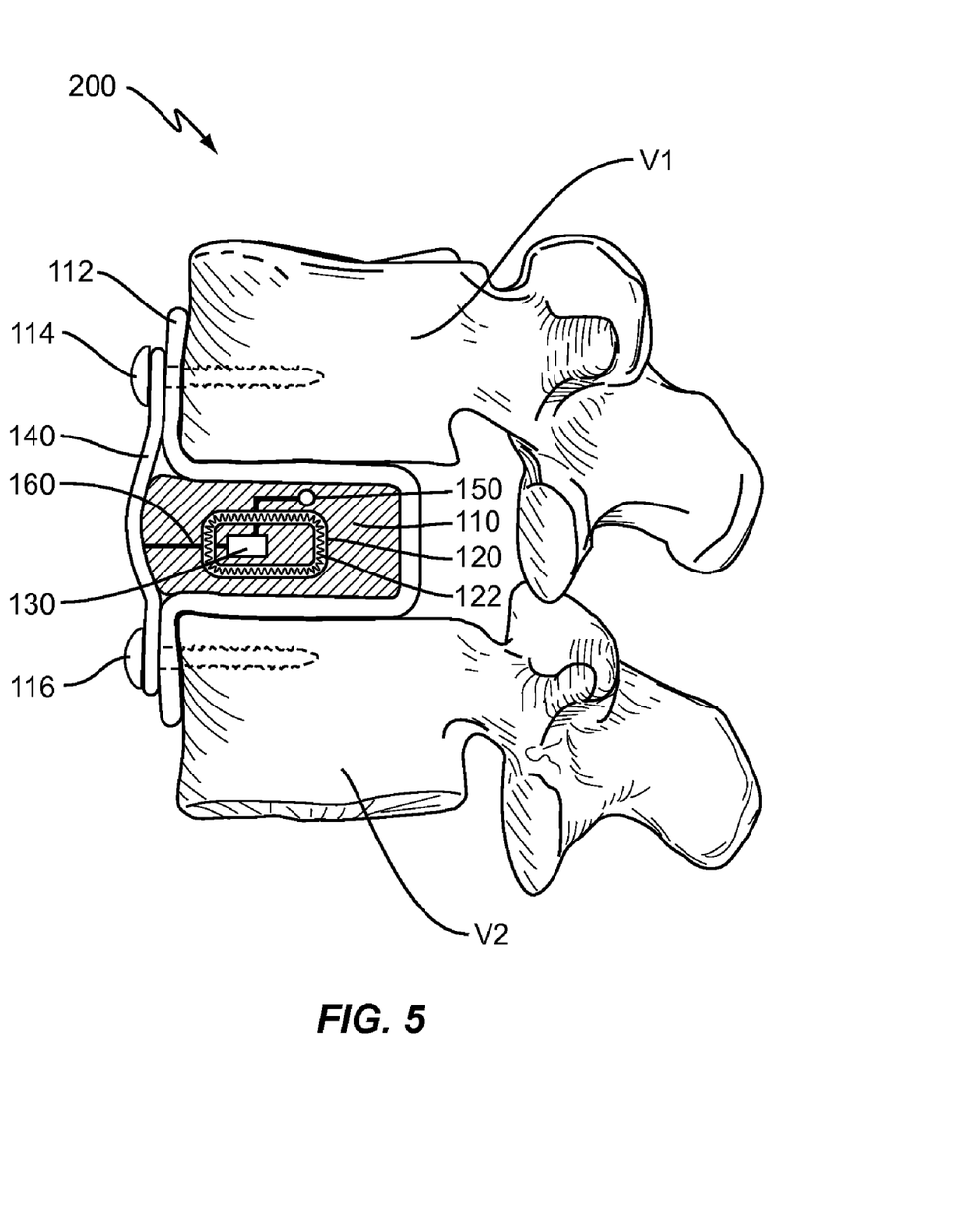
FIG. 5 shows a side view of the diagnostic system of FIG. 3 after its activator has been activated in the opposite manner displayed in FIG. 4.

Alternatively, if less pressure is needed for the implant 110 to accomplish its desired task, the system 200 can cause the activator to bend in the opposite direction of that shown in FIG. 4. For example, as shown in FIG. 5, the activator 140 is flexed or bent outward, i.e., away from the implant 110, thereby reducing pressure on the implant 110. In each of the embodiments of FIGS. 4 and 5, the activator 140 may be designed only to be move in one direction, e.g., when the temperature of the shape memory alloy is increased, but it is possible that a decrease in the alloy can cause the activator 140 to bend in the opposite direction, and therefore, be able to both increase or decrease pressure on the implant 110. Also note that by decreasing the temperature from that taken to achieve the state shown in FIG. 5, the activator 140 can revert to its shape shown in FIG. 3 (and the same is true for reverting from the state of FIG. 4 to the state shown in FIG. 3). Furthermore, it is possible to have the activator 140 to have various forms that are achieved at different temperature increases so that one can change the shape of the activator 140 (and thereby the pressure on the implant 110) in an incremental fashion.

Figure 6:
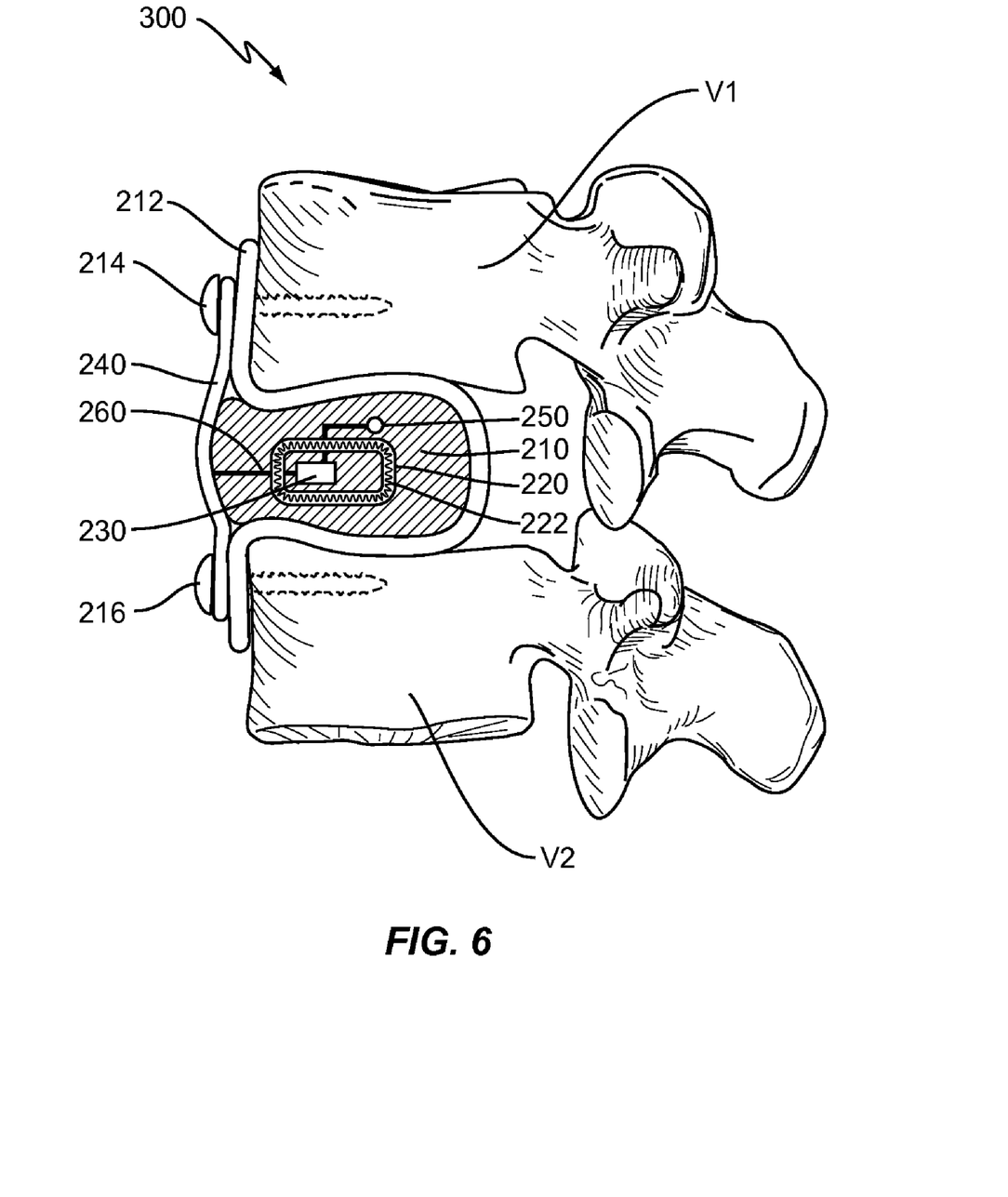
FIG. 6 shows a side view of another embodiment of the diagnostic measuring, monitoring and response system of the present invention after the activator and portion of the containment portion have been activated.

FIG. 6 shows a side view of another embodiment of the diagnostic measuring, monitoring and response system 300 ("diagnostic system") of the present invention. The diagnostic system 300 of FIG. 3 comprises an implant 210, a fabric material 220, an antenna 222, a sensor 230, an activator 240, a power source 250, and a network 260 that electrically connects all of these components. As shown in FIG. 6, the implant 210 also is encapsulated (although not entirely) by a containment portion 212, and in part, by the activator 240, which serves, in part, as a separate cover portion. Note, once again, that the implant 210 is not limited to the shape shown in FIG. 6, but may be any shape to occupy the intervertebral disc space S, or even part of the disc space S.

The diagnostic system 300 of FIG. 6 is similar to the system 200 of FIG. 3, although has one difference. With the diagnostic system 300, the containment portion 240 also can act as an activator 240 (i.e., be comprised of or contain a shape memory alloy such as NiTi and act in the same fashion as the activator 140) in that it will help respond to signals coming in to the antenna 222 from the doctors or surgeons. For example, as shown in FIG. 6 (and compared to a starting point shown similar to that of FIG. 3), the containment portion 212 has expanded, thereby providing more physical space for the implant 210, thereby helping to reduce pressure on the implant 210, i.e., in addition to the activator 240. Accordingly, the main difference from the system 200 of FIG. 5 compared to the system 300 of FIG. 6 is that it has an additional activating component in that of the containment portion 212. Similarly, with a different desired shape for the activator 240 and the containment portion 212, the system 300 can be designed to increase pressure on the implant 210, similar to the system 200 of FIG. 4. Further, in such a system 300, it is an optional whether the activator 240 or the additional activating component in the containment portion 212 are activated, or if both are activated, or just as with system 100, to what extent each may be activated.

Note also, that with such a system 300 of FIG. 6, there may be a direct connection of the network 260 from the battery to the containment portion 212. Further, it is most likely that the entire containment portion would not be composed of or contain shape memory alloy materials. That is, in such embodiment, it is not desirable for the portion of the containment portion 212 that is necessary for screws 214 and 216 to affix the containment portion 212 to the vertebrae V1 and V2 to change shape.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. As stated, the present invention may be used anywhere in the human body, or in any orthopedic situation. For example, in addition to the context described above and shown FIGS. 2-6, the present invention may be used in a diagnostic system of the present invention in the context of a multi-level rod system or a corpectomy device. Accordingly, those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed:

1. A diagnostic system for a spinal implant, the system comprising:
    a spinal implant adapted to be situated within a disc space between two adjacent vertebrae;
    a containment portion adapted to separate the spinal implant from the disc space and extend therefrom and attach to an anterior surface of the adjacent vertebrae, said containment portion defining an opening oriented to face the anterior surface;
    an antenna located in, on or adjacent to the spinal implant for sending and/or receiving signals to and/or from a remote location;
    a sensor located in, on or adjacent to the spinal implant for measuring at least one diagnostic condition in, on or adjacent to the implant;
    an activating element located in, on or adjacent to the spinal implant that has the ability to affect the at least one diagnostic condition, said activating element positioned across and sealing said opening;
    a power source located in, on or adjacent to the spinal implant to provide power to the diagnostic system; and
    a network that electrically connects the antenna, sensor, activating element and power source.

2. The diagnostic system of claim 1, wherein the antenna is incorporated into a material that can be integrated into the spinal implant.

3. The diagnostic system of claim 1, wherein the antenna is woven or interlaced in a fabric material.

4. The diagnostic system of claim 2, wherein the antenna and fabric material are incorporated into the spinal implant.

5. The diagnostic system of claim 1, wherein:
    the at least one diagnostic condition may be any one of the following indicia: loading information, pressure information, tension information, motion information, alignment or misalignment information, or temperature.

6. The diagnostic system of claim 1, wherein:
    the activating element is such that the diagnostic system is capable of affecting the at least one diagnostic condition incrementally and/or in either direction.

7. The diagnostic system of claim 1, wherein:
    the activating element is one of the following devices: a hydrostatic pump or a shape memory alloy.

8. The diagnostic system of claim 6, wherein:
the activating element is a shape memory alloy and includes a device to increase temperature, wherein such device is connected to the shape memory alloy and is controlled by the addition or subtraction of power or electrical signals.

9. The diagnostic system of claim 1, wherein:
the implant is made of a flexible material.

10. A diagnostic system for the human body, the system comprising:
an implant adapted to be situated in the human body;
an antenna located in, on or adjacent to the implant for sending and/or receiving signals to and/or from a remote location;
a sensor located in, on or adjacent to the implant for measuring at least one diagnostic condition in, on or adjacent to the implant, the at least one diagnostic condition including one or more of the following indicia: loading information, pressure information, tension information, or temperature;
an activating element located in, on or adjacent to the implant that has the ability to affect the at least one diagnostic condition;
a power source located in, on or adjacent to the implant to provide power to the diagnostic system; and
a network that electrically connects the antenna, sensor, activating element and power source.

11. The diagnostic system of claim 10, wherein the implant is an orthopedic implant.

12. The diagnostic system of claim 10, wherein the antenna is woven or interlaced in a fabric material.

13. The diagnostic system of claim 12, wherein the antenna and fabric material are incorporated into the implant.

14. The diagnostic system of claim 10, wherein:
the at least one diagnostic condition may also include one or more of the following indicia: motion information or alignment or misalignment information.

15. The diagnostic system of claim 10, wherein the implant is made of a flexible material.

16. The diagnostic system of claim 10, wherein:
the activating element is such that the diagnostic system is capable of affecting the at least one diagnostic condition incrementally and/or in either direction.

* * * * *